US00PP14994P2

(12) United States Plant Patent
Drewlow

(10) Patent No.: US PP14,994 P2
(45) Date of Patent: Jul. 6, 2004

(54) POINSETTIA PLANT NAMED 'GALA RED'

(50) Latin Name: *Euphorbia pulcherrima*
Varietal Denomination: Gala Red

(75) Inventor: Lyndon W. Drewlow, Lompoc, CA (US)

(73) Assignee: Olgevee Ltd., Connellsville, PA (US)

( * ) Notice: Subject to any disclaimer, the term of this patent is extended or adjusted under 35 U.S.C. 154(b) by 0 days.

(21) Appl. No.: 10/666,274

(22) Filed: Sep. 17, 2003

(51) Int. Cl.[7] ..... A01H 5/00
(52) U.S. Cl. ..... Plt./307
(58) Field of Search ..... Plt./307

*Primary Examiner*—Kent Bell
*Assistant Examiner*—June Hwu
(74) *Attorney, Agent, or Firm*—C. A. Whealy

(57) ABSTRACT

A new and distinct cultivar of Poinsettia plant named 'Gala Red', characterized by its compact, uniform and upright plant growth habit; strong lateral branches; freely branching habit; dark green-colored leaves; inflorescences with dark red-colored flower bracts that resist fading; and excellent post-production longevity.

1 Drawing Sheet

Botanical classification/cultivar denomination: *Euphorbia pulcherrima* Willd. cultivar Gala Red.

BACKGROUND OF THE INVENTION

The present Invention relates to a new and distinct cultivar of Poinsettia plant, botanically known as *Euphorbia pulcherrima* Willd., and hereinafter referred to by the cultivar name 'Gala Red'.

The new Poinsettia is a product of a planned breeding program conducted by the Inventor in Ashtabula, Ohio and Lompoc, Calif. The objective of the breeding program is to create new Poinsettia cultivars with upright and uniform plant habit and attractive flower bract coloration.

The new Poinsettia originated from a cross-pollination made by the Inventor in 1996 in Ashtabula, Ohio of a proprietary Poinsettia seedling selection identified as 92-218-3, not patented, as the female, or seed, parent with the Poinsettia cultivar Fiscor, disclosed in U.S. Plant Pat. No. 9,364, as the male, or pollen, parent. The new Poinsettia was discovered and selected by the Inventor as a flowering plant within the progeny of the stated cross-pollination in a controlled environment in Lompoc, Calif. in 1998.

Asexual reproduction of the new Poinsettia by vegetative terminal cuttings taken at Lompoc, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Gala Red'. These characteristics in combination distinguish 'Gala Red' as a new and distinct Poinsettia cultivar:

1. Compact, uniform and upright plant growth habit.
2. Strong lateral branches.
3. Freely branching habit.
4. Dark green-colored leaves.
5. Inflorescences with dark red-colored flower bracts that resist fading.
6. Excellent post-production longevity.

Plants of the new Poinsettia differ primarily from plants of the female parent selection primarily in plant growth habit.

Plants of the new Poinsettia can be compared to plants of the male parent, the cultivar Fiscor. In side-by-side comparisons conducted in Lompoc, Calif., plants of the new Poinsettia differed from plants of the cultivar Fiscor in the following characteristics:

1. Plants of the new Poinsettia had larger leaves than plants of the cultivar Fiscor.
2. Plants of the new Poinsettia flowered about 3.5 to 7 days earlier than plants of the cultivar Fiscor.
3. Plants of the new Poinsettia had darker red-colored flower bracts than plants of the cultivar Fiscor.
4. Plants of the new Poinsettia tolerated high night temperatures better than plants of the cultivar Fiscor.

Plants of the new Poinsettia can be compared to cultivar Fiscor Dark Red, disclosed in U.S. Plant Pat. No. 12,723. In side-by-side comparisons conducted in Lompoc, Calif., plants of the new Poinsettia differed from plants of the cultivar Fiscor Dark Red in the following characteristics:

1. Plants of the new Poinsettia were more upright and had stronger lateral branches than plants of the cultivar Fiscor Dark Red.
2. Plants of the new Poinsettia had shorter and thicker leaf petioles than plants of the cultivar Fiscor Dark Red.
3. Plants of the new Poinsettia flowered about 3.5 to 7 days earlier than plants of the cultivar Fiscor Dark Red.
4. Plants of the new Poinsettia had darker red-colored flower bracts than plants of the cultivar Fiscor Dark Red.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia. The photograph comprises a top perspective view of a single flowering plant of 'Gala Red' grown in a container.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photograph and following observations and measurements describe plants grown in Lompoc, Calif. during the fall and winter under commercial practice in a fiberglass-covered greenhouse with day temperatures ranging from 18 to 21° C., night temperatures ranging from 16.5 to 18° C., and light levels about 3,000 to 4,000 foot-candles. Single plants were grown in 15-cm pots, pinched once, and flowered under controlled short day/long night conditions. Plants were about 16 weeks from unrooted cuttings when the aforementioned photograph and the following detailed botanical description were taken. In the following description, color references are made to The Royal Horticultural Society Colour Chart, 1995 edition, except where general terms of ordinary dictionary significance are used.

Botanical classification: *Euphorbia pulcherrima* Willd. cultivar Gala Red.

Parentage:

*Female, or seed, parent.*—Proprietary selection of *Euphorbia pulcherrima* identified as code number 92-218-3, not patented.

*Male, or pollen, parent.*—*Euphorbia pulcherrima* cultivar Fiscor, disclosed in U.S. Plant Pat. No. 9,364.

Propogation:

*Type cutting.*—Vegetative terminal cuttings.

*Time to initiate roots.*—Summer: About 14 days at 21° C. Winter: About 18 days at 21° C.

*Time to produce rooted young plants.*—Summer: About 21 days at 21° C., Winter: About 25 days at 21° C.

*Root description.*—Thick, fibrous and freely-branching.

Plant description:

*Growth habit.*—Compact, upright and uniform plant habit; inverted triangle; vigorous.

*Plant height.*—About 26 to 28 cm.

*Plant diameter or spread.*—About 45 to 50 cm.

*Lateral branch description.*—Quantity: Plants pinched to five to six leaves develop one lateral branch per node. Length: About 25 cm. Diameter: About 7 mm. Internode length: About 2 cm. Strength: Strong. Texture: Smooth, glabrous. Color: 146A.

*Foliage description.*—Arrangement: Alternate, simple. Length: About 12 to 13 cm. Width: About 9 to 10 cm. Shape: Ovate with deep lobing. Apex: Acuminate to acute. Base: Acute. Margin: Entire with lobing. Venation pattern: Pinnate. Texture, upper and lower surfaces: Glabrous, smooth. Color: Developing foliage, upper and lower surfaces: 146C. Fully expanded foliage, upper surface: 147A. Fully expanded foliage, lower surface: 147B. Venation, upper surface: 147B. Venation, lower surface: 147C. Petioles: Length: About 5.5 to 6 cm. Diameter: About 3 mm. Texture: Glabrous, smooth. Color: 185A.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under short day/long night conditions. Relatively early flowering; response time, about 8 to 8.5 weeks, under controlled photoperiod conditions.

*Post-production longevity.*—Plants of the new Poinsettia maintain good substance and bract color for more than six weeks under interior conditions.

*Quantity of inflorescences.*—One per lateral branch.

*Inflorescence diameter.*—About 30 cm.

*Inflorescence height.*—About 2 to 3 cm.

*Flower bracts.*—Quantity of flower bracts: About 15 to 20 per inflorescence. Length, largest bracts: About 12 to 13 cm. Width, largest bracts: About 7 to 8 cm. Shape: Ovate. Apex: Acuminate. Base: Acute. Margin: Entire. Texture, upper and lower surfaces: Glabrous, smooth. Orientation: Mostly horizontal. Color: Developing bracts, upper surface: 46A. Developing bracts, lower surface: 45A. Fully developed bracts, upper surface: 45A; color becoming closer to 45B with development. Fully developed bracts, lower surface: 46B. Bract petioles: Length: About 1 to 2.5 cm. Diameter: About 2 mm. Texture: Glabrous, smooth. Color: 46A.

*Cyathia.*—Quantity of cyathia: About 10 to 15 per corymb. Diameter of cyathia cluster: About 3 cm. Shape: Rounded. Length: About 1 cm. Diameter. About 5 mm. Color, immature: 146C. Color, mature: 146B. Stamens: Quantity of stamens: More than 50 per cyathium. Anther shape: Oblong. Anther length: About 1 mm. Anther color: 185A. Pollen amount: Abundant. Pollen color: 12A. Pistils: Quantity of pistils: One per cyathium. Pistil length: About 8 mm. Style length: About 2 mm. Style color: 146D. Stigma color: 185A. Ovary color: 146D. Nectaries: Quantity of nectaries: One or two per cyathium. Width: About 4 mm. Color: 17A.

Disease/pest resistance: Plants of the new Poinsettia have not been observed to be resistant to pathogens and pests common to Poinsettias.

It is claimed:

1. A new and distinct cultivar of Poinsettia plant named 'Gala Red', as illustrated and described.

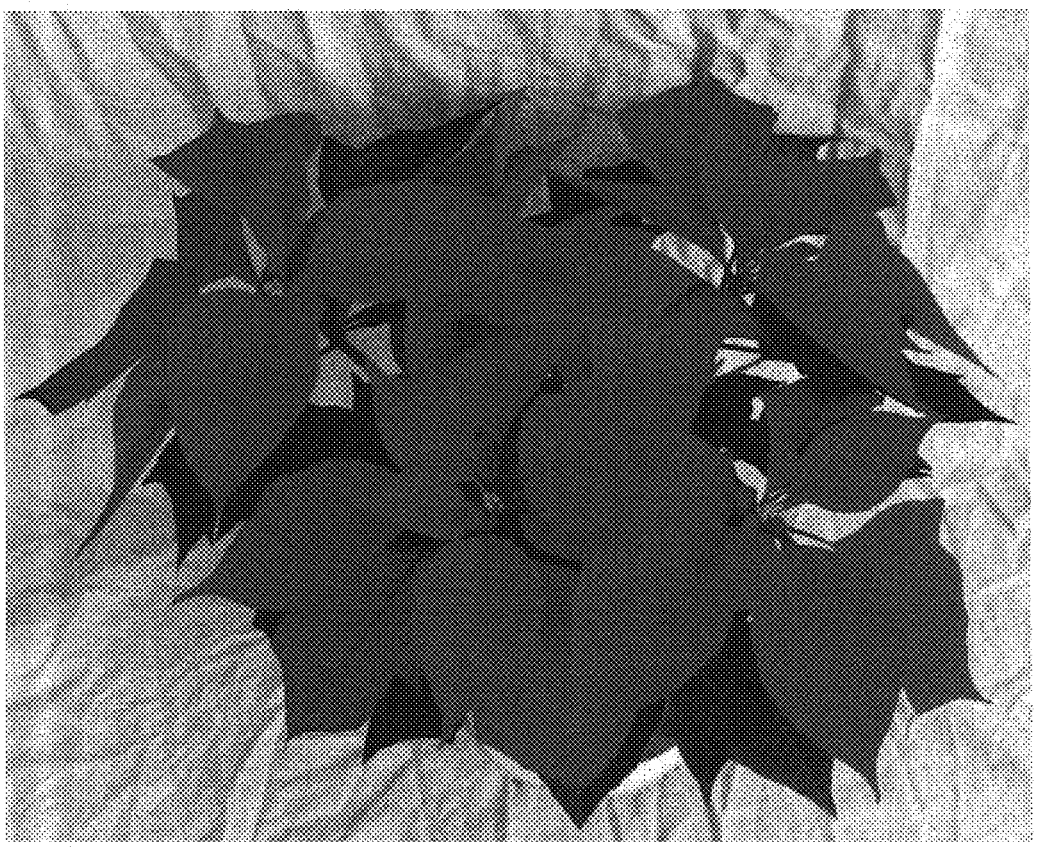

* * * * *